United States Patent [19]
Benson

[11] 4,182,344
[45] Jan. 8, 1980

[54] PRESSURE CONTROL TRACHEAL DEVICE

[75] Inventor: Gerald B. Benson, Gt. Missenden, England

[73] Assignee: G. D. Searle & Co., Limited, High Wycombe, Bucks, England

[21] Appl. No.: 825,879

[22] Filed: Aug. 19, 1977

[51] Int. Cl.² ............... A61M 25/00; A61M 16/00
[52] U.S. Cl. .................. 128/207.15; 60/413; 60/418; 138/30; 138/31; 340/626
[58] Field of Search ................. 128/348–351; 138/26, 30, 31; 60/413, 418; 340/626

[56] References Cited
U.S. PATENT DOCUMENTS

| | | | |
|---|---|---|---|
| 2,015,436 | 9/1935 | Nemes et al. | 138/31 |
| 3,048,171 | 8/1962 | Grau | 128/214.2 |
| 3,050,003 | 8/1962 | Edwards | 417/12 |
| 3,674,010 | 7/1972 | Falenks | 128/2 R |
| 3,677,334 | 7/1972 | Bathla et al. | 138/31 X |
| 3,794,043 | 2/1974 | McGinnis | 128/351 |
| 4,014,213 | 3/1977 | Parquet | 138/31 X |
| 4,079,736 | 3/1978 | Lundquist | 128/214 R |
| 4,119,101 | 10/1978 | Igich | 128/351 |
| 4,134,407 | 1/1979 | Elam | 128/351 |

Primary Examiner—Dalton L. Truluck
Attorney, Agent, or Firm—James R. Henes; John A. Dhuey

[57] ABSTRACT

A device for controlling the pressure in an inflatable cuff surrounding an endotracheal or tracheostomy tube is described.

8 Claims, 3 Drawing Figures

PRESSURE CONTROL TRACHEAL DEVICE

The present invention relates generally to pressure in an inflatable cuff surrounding an endotracheal or tracheostomy tube.

When a patient is anaesthetized it is normal clinical practice to pass an endotracheal tube into the trachea and connect the endotracheal tube to a breathing machine. In order to ensure that aspiration cannot occur when the endotracheal tube is in place, the breathing tube is surrounded by an inflatable cuff which is connected to an inflation tube. When the breathing tube is in place, the cuff is inflated so as to affect a gas tight seal against the tracheal wall and prevent aspiration of secretions. Ideally, the cuff should be inflated with sufficient pressure to effect a seal but no more. This point is difficult to identify when the patient is breathing spontaneously. During anaesthesia the trachea relaxes and there is therefore a tendency to inflate the cuff a little more than is necessary to effect a seal. In addition it has been found that a small increase in the injected volume of gas causes a large increase in pressure within the cuff thus increasing the pressure applied to the wall of the trachea.

If the pressure applied to the wall of the trachea is too great it causes damage as a result of restriction of the blood circulation. Damage can occur after a relatively short time and the severity is proportional to the duration of contact. This damage which is known as "cuff stenosis" occurs if the pressure exerted by the cuff on the trachea exceeds the blood capillary pressure within the wall and the condition is aggravated by hypotension, steroid treatment and many other factors.

It has also been found that the breathing tube tends to reciprocate in the trachea as the longitudinal force applied to the cuff by the breathing tube varies. This can result in the tip of the breathing tube causing erosion of the wall of the trachea.

It will be seen therefore that it is of the utmost importance to ensure that the pressure applied to the inflatable cuff of a tracheal breathing tube is correct and is maintained at a constant value.

With these objects in mind we provide in accordance with the present invention a pressure controlling device for an inflatable cuff comprising a fluid reservoir, an outlet from the fluid reservoir for connection to the inflatable cuff and means for maintaining a constant fluid pressure in the reservoir so as to compensate for changes in the factors determining the pressure in the cuff thereby ensuring a constant fluid pressure within the cuff.

The means for maintaining a constant pressure in the reservoir may comprise a piston defining a wall of the reservoir and movable under gravity within the reservoir. Alternatively, a flexible diaphragm may be provided which is movable under the bias of a constant pressure biassing means to vary the volume of the reservoir.

In use, the inflation tube of an inflatable cuff is connected to the outlet from the reservoir, the reservoir is charged with air and the pressure in the cuff is then determined by the constant pressure means, which may comprise the piston or the diaphragm. As the factors which determine the pressure in the cuff vary, the volume of the reservoir will change in response to the pressure applied by the piston or the diaphragm thereby ensuring that the pressure within the cuff remains constant.

The dimensions of the reservoir are chosen to ensure that there is sufficient reserve volume of air to allow for loss as a result of leakage and diffusion from the inflated cuff over a period of several hours. It has been suggested that 15–20 Torr (20–27 cm water) is the optimum cuff pressure for a large volume tracheal tube cuff and the weight of the piston or the strength of the diaphragm spring is so selected that the pressure in the system will equal approximately 20 Torr.

In a preferred embodiment of the invention, a warning device, which may be a visible or audible warning device, is actuated when the volume of fluid in the reservoir falls below a predetermined value. This will ensure that the reservoir is always recharged before the point is reached at which there is a danger of the pressure in the cuff falling below a value which will ensure a seal against the trachea wall.

A preferred form of the present invention will now be described with reference to the accompanying drawings in which.

Figure 1:
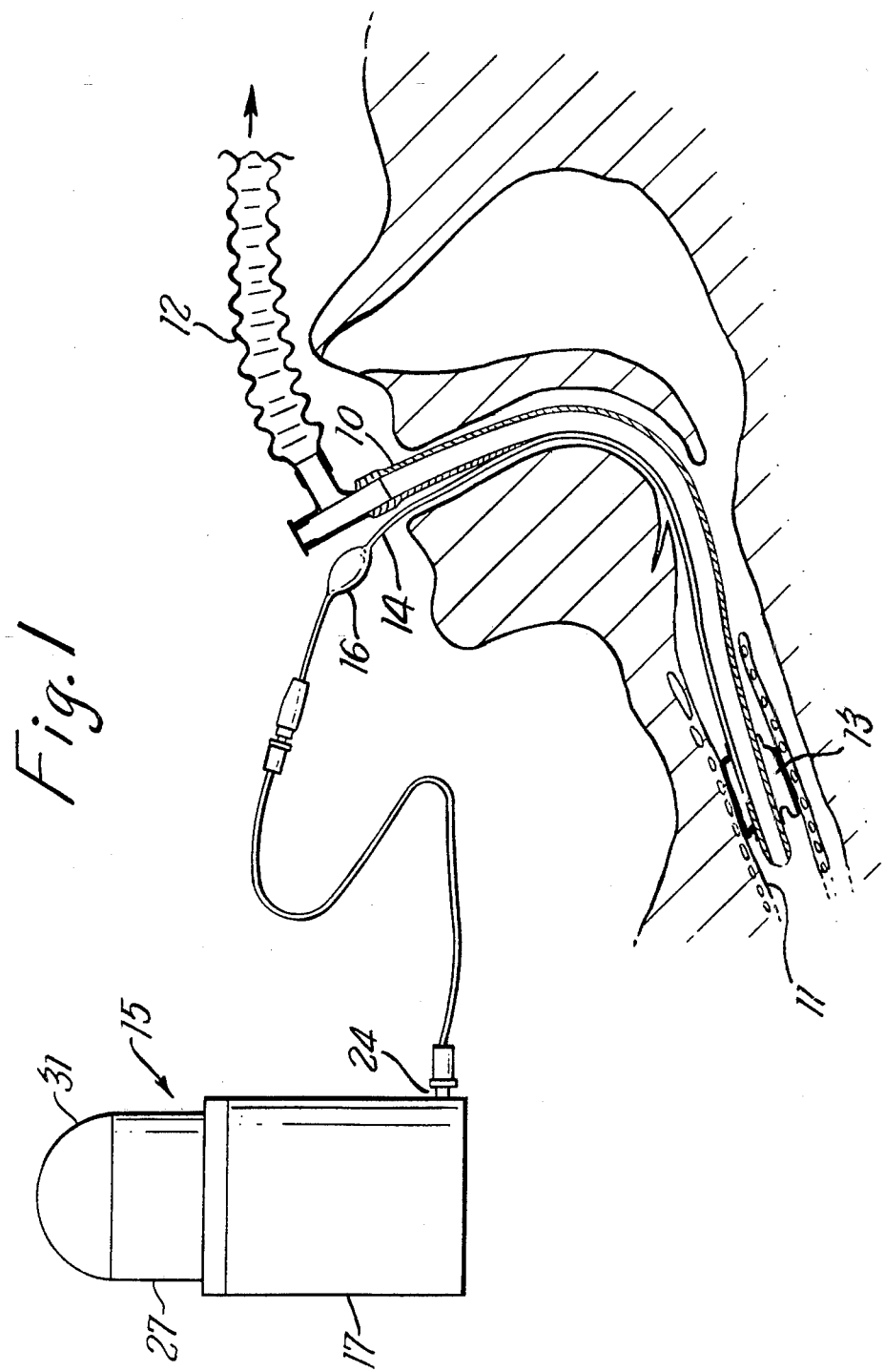
FIG. 1 is a diagrammatic illustration of a tracheal breathing tube in place within a trachea and surrounded by an inflated cuff connected to a pressure controlling device according to the present invention.
Figure 2:
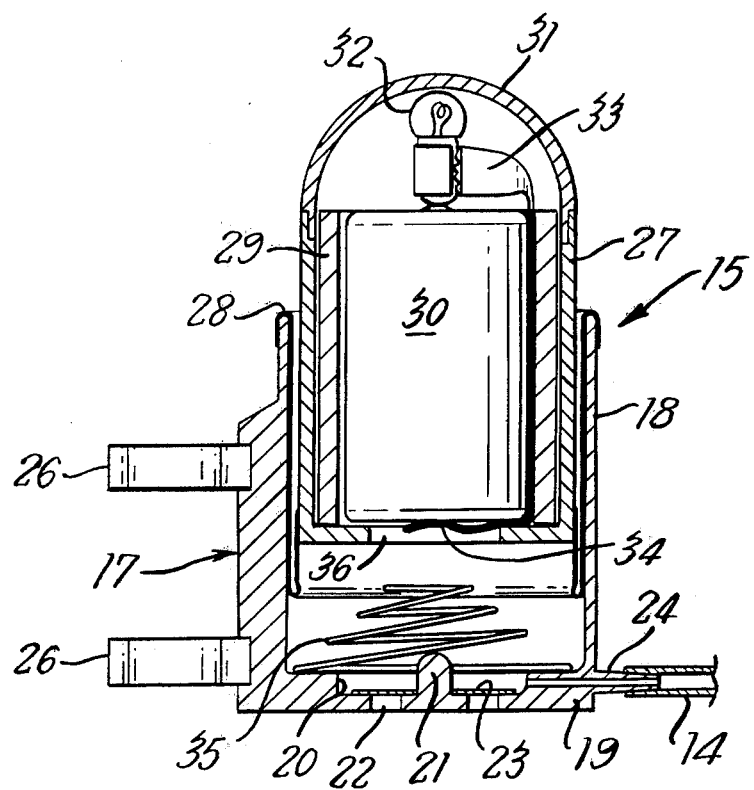
FIG. 2 is a section through the pressure controlling device shown in FIG. 1.

In FIG. 1 a tracheal breathing tube 10 is shown inserted into the trachea 11 of a patient and connected via a tube 12 to a breathing machine.

The end of the breathing tube 10 which is located within the trachea 11 is surrounded by an inflatable cuff 13 which is connected via an inflation tube 14 to a pressure controlling device 15. When the breathing tube 10 is in place within the trachea 11, the cuff 13 is inflated to a pressure of approximately 15–20 Torr so as to form a seal against the wall of the trachea and prevent aspiration of fluid in either direction along the trachea. A pilot bulb 16 is provided at the outer end of the inflation tube as a visual indication of the approximate pressure in the cuff 13.

Hitherto a pumping device such as a syringe was provided to inflate the cuff 13, the pressure in the cuff 13 being judged by feeling the pressure in the pilot bulb 16. This can be an inaccurate method of determining the pressure in the cuff 13 and often results in damage to the tracheal wall. The pilot bulb 16 also acted hitherto as an indication of any pressure drop in the cuff 13. This meant that the pilot bulb 16 has to be tested periodically and pumped up to the required pressure whenever necessary.

The pressure controlling device 15 of the present invention is intended to obviate the necessity for manually pumping the inflation tube 14 so as to inflate the cuff 13 and to provide an accurate and permanent pressure in the cuff 13.

The pressure controlling device 15 comprises a reservoir 17 comprising a cylindrical wall 18 and a substantially flat bottom wall 19. The bottom wall 19 is formed with a central recess 20, an upwardly projecting central boss 21 and a plurality of apertures 22. A valve disc 23 is located in the recess 20 so as to close the aperture 22 and acts as a one way flap valve. An outlet 24 is provided through the bottom wall 19 at a point just above the valve disc 23. Clips 26 are also mounted on the wall 18 of the reservoir for attaching the device to a support.

A hollow cylindrical piston 27 is mounted within the reservoir 17 and connected to the wall 18 of the reservoir by a flexible rolling diaphragm 28. The diaphragm 28 provides a seal between the piston 27 and the wall of the reservoir 17 but allows the piston 27 to rise and fall within the reservoir with a minimal frictional interference.

The piston 27 forms a housing for a weight 29 and a battery 30. The upper end of the piston 27 comprises a translucent dome 31 within which is mounted a bulb 32 held by a metallic bulb mounting strip 33. The strip 33 extends down one side of the battery 30 and beneath the bottom of the battery, where it is spaced from the bottom of the battery by an insulated pad 34. A light spring 35 is located between the base 19 of the reservoir and the piston 27, the upper end of the spring 35 being adapted to pass through an aperture 36 in the base of the reservoir and press the strip 33 against the base of the battery when the piston sinks below a predetermined point in the reservoir, thereby completing a circuit to the bulb.

In use, the inflation tube 14 of the cuff 13 is connected to the outlet 24 of the device 15. The piston 27 is then raised so as to draw the valve disc 23 upwardly and draw air into the reservoir through the apertures 22. The piston is then released so that its weight applies pressure to the air within the reservoir, closing the disc valve 23 and applying pressure to the inflation tube 14 and cuff 13.

The total weight of the piston 27 and the components housed within the piston 27 is selected to ensure that the pressure applied to the cuff 13 is within the range 15-20 Torr. Consequently, all that is necessary, in order to inflate the cuff 13 to the required pressure is to raise the piston 27 and release it.

As leakage and diffusion of air from the inflation tube 14 and cuff 13 occur the piston will sink within the reservoir but the pressure within the cuff 13 will be maintained at a constant value. If the piston 27 sinks to the point in the reservoir at which the spring 35 presses the strip 33 into contact with the bottom of the battery 30 the bulb 32 will light up giving a visual warning that the reservoir requires recharging. All that is necessary to recharge the reservoir is to lift the piston and release it.

It has been found that changes in the volume of the cuff 13 which may be caused either by relaxation of the trachea or changes in the pressure within the breathing tube 10 are accommodated by the pressure controlling device 15 and result in negligible changes in the pressure within the cuff.

It has also been noted that the maintenance of a constant pressure within the cuff 13 results in less longitudinal movement of the breathing tube 10 in the trachea in response to the cylical changes of pressure within the breathing tube iritating and eroding the tracheal wall.

The incorporation of an inlet valve in the device 15 is not essential and the bottom wall 19 of the reservoir can be imperforate, the reservoir being recharged by disconnecting the inflation tube 14 from the outlet 24, raising the piston 27 to recharge the reservoir, reconnecting the inflation tube 14 to the outlet 24 and then releasing the reservoir 27. Alternatively any different form of one way valve may be provided in place of the disc valve 23.

It will also be appreciated that the warning device is not essential, or alternatively that any other convenient form of warning device can be provided to give either a visable or an audible warning that the piston is reaching the bottom of the reservoir. Alternatively the pressure in the pilot bulb 16 may be used as a waring that the pressure provided by the pressure controlling device 15 is falling below the required value.

It is also envisaged that alternative sealing means between the piston and the reservoir may be employed although the advantages of the rolling diaphragm are substantial as it is virtually frictionless.

Figure 3:
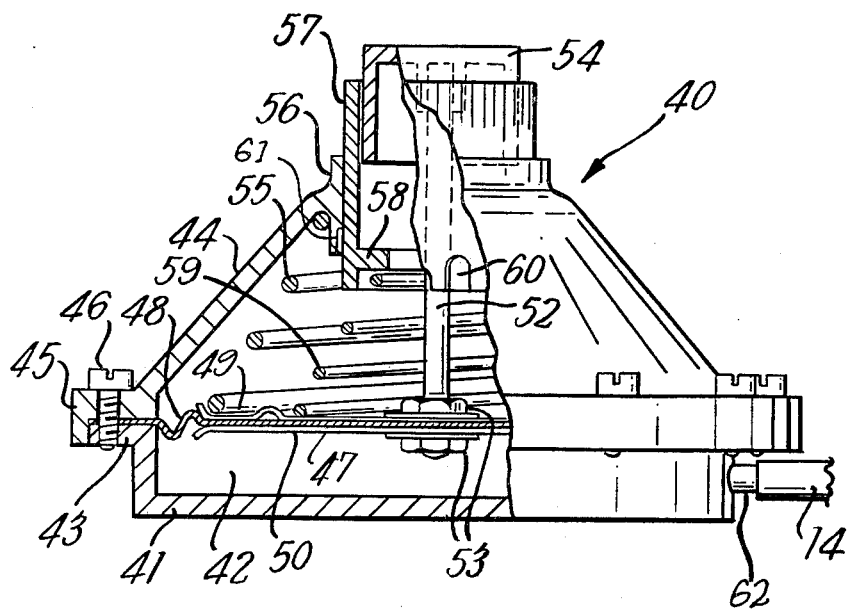
FIG. 3 is a section through an alternative pressure controlling device in accordance with the present invention.

An alternative pressure controlling device is indicated generally at 40 in FIG. 3 which has the advantage over the device 15 that it enables the pressure setting in the reservoir to be easily and accurately varied.

The pressure controlling device 40 comprises a lower housing 41 forming a generally cylindrical reservoir 42 and having an outwardly directed flange 43. An upper housing 44 has a peripheral L-section flange 45 which rests on the flange 43 of the lower housing 41 and is attached thereto by screws 46. A flexible diaphragm 47 has its peripheral edge trapped between the flanges 43 and 45 and forms an end wall of the reservoir 42. The diaphragm 47 has circumferential corrugations 48 to provide free movement of the diaphragm and upper and lower stiffening discs 49 and 50 respectively.

Attached to the discs 49, 50 by a rod 52 and nut 53, is a cylindrical cap 54, the movement of which will accurately reflect movement of the diaphragm 47 in the reservoir 42.

A zero rated spring 55 is mounted between the upper plate 49 on the diaphragm 47 and a boss 56 at the upper end of the upper housing 44. The spring 55 applies a constant pressure on the diaphragm disc 49 throughout the full working range of the diaphragm. Vertically, slidably housed within the boss 56 is a sleeve 57 having an internal flange 58. Located between the flange 58 and the upper disc 49 of the diaphragm is a spring 59. The bottom end of the sleeve 57 is formed with a plurality of outwardly projecting lugs 60 which normally locate within recesses 61, in the inner surface of the boss 56. When the lugs 60 are located in the recesses 61 in the boss 56, the position of the sleeve 57 relative to the boss 56 is such that the spring 59 is in a relaxed condition.

It it is required to increase the pressure applied to the diaphragm 47, the sleeve 57 is depressed to take the lugs 60 out of engagement with the recesses 61 and rotated so that the lugs 60 locate on the bottom edge of the boss. This causes compression of the spring 59 between the flange 58 and the upper disc 49, thereby increasing the loading on the diaphragm 47.

In use, an outlet 62 from the reservoir 42 is connected to the inflation tube 14 of the cuff 13 and thereafter the pressure in the cuff will be determined by the pressure applied by the spring 55 and 59 on the diaphragm 47. Any changes in pressure in the cuff will be taken up by movement of the diaphragm 47 so as to ensure that a constant pressure is maintained in the reservoir and within the cuff. Means may be provided for injecting fluid into the reservoir to compensate for leakage of fluid from the system. This may be accomplished by the provision of a one way inlet valve in a wall of the reservoir or by any other suitable means.

If it becomes necessary to increase the pressure in the cuff, all that is necessary is to depress the sleeve 57 and rotate the sleeve so as to bring the second spring 59 into operation.

It will be appreciated that any number of concentric springs and sleeves similar to the spring 59 and the sleeve 57 may be incorporated in the device 40 to provide any required number of different settings.

The setting can be read from a scale provided on the cap 54 and any suitable warning device may be incorporated in the device to give a warning if the pressure in the reservoir falls below a predetermined value.

It is envisaged that an adjusting screw may be provided for varying the height of the main spring 55 so as to provide variations in the load on the diaphragm. The height of the spring can be read from a scale provided on the device so as to give a visual indication of the setting on the diaphragm 47. In this way the pressure in the reservoir 42 is adjustable but is substantially constant at any one selected setting.

What is claimed is:

1. A pressure controlled tracheal device comprising in combination:
   (a) a fluid reservoir having a variable volume and an outlet;
   (b) a tracheal tube having a first end and a second end, said first end adapted for connection to a source of respiratory gas;
   (c) an inflatable cuff in fluid communication with the outlet of said reservoir and attached around and adjacent to the second end of said tracheal tube;
   (d) means for maintaining a constant fluid pressure in said reservoir; and
   (e) warning means responsive to the volume of said reservoir and actuable when the volume of said reservoir reaches a predetermined value.

2. A device as claimed in claim 1, wherein the means for maintaining a constant fluid pressure in the reservoir comprises a piston defining a wall of the reservoir movable under gravity within the reservoir so as to change the volume of the reservoir in response to pressure changes at the outlet thereby maintaining a constant pressure within the reservoir which is determinable by the weight of the piston.

3. A device as claimed in claim 2, wherein the piston is sealed against the adjacent wall of the reservoir by a resilient skirt which forms a rolling seal.

4. A device as claimed in claim 3, wherein a one way inlet valve is provided in the reservoir whereby the reservoir can be recharged by raising the piston to draw fluid into the reservoir through the one way valve.

5. A device as claimed in claim 1, wherein the means for maintaining a constant pressure in the fluid in the reservoir comprises a flexible diaphragm which forms a wall of the reservoir and which is movable under the bias of a constant pressure biassing means to change the volume of the reservoir in response to changes in pressure at the outlet thereby maintaining a constant pressure within the reservoir determinable by the strength of the biassing means.

6. A device as claimed in claim 5, wherein the biassing means comprises a constant pressure coil spring.

7. A device as claimed in claim 1 wherein the warning device gives a visual indication of the volume of the reservoir at any given time.

8. A device as claimed in claim 7, wherein the warning device comprises a scale and a pointer, one of which is movable relative to the other as the volume of the reservoir changes.